United States Patent [19]
Matumoto et al.

[11] Patent Number: 6,059,722
[45] Date of Patent: *May 9, 2000

[54] LIGHT SOURCE DEVICE FOR ENDOSCOPE WHICH IS CAPABLE OF LIGHT SETTING SHADING PERIOD

[75] Inventors: Seiji Matumoto, Omiya; Suwao Satoh, Okaya; Fujio Okada; Shigeo Suzuki, both of Omiya, all of Japan

[73] Assignee: Fuji Photo Optical Co., Ltd., Saitama, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/950,587

[22] Filed: Oct. 15, 1997

[30] Foreign Application Priority Data

Oct. 23, 1996  [JP]  Japan ................................. 8-299712

[51] Int. Cl.$^7$ ...................................................... A61B 1/06
[52] U.S. Cl. ............................................ 600/178; 348/68
[58] Field of Search .................................. 600/178, 180; 348/68, 69

[56] References Cited

U.S. PATENT DOCUMENTS

| | | | |
|---|---|---|---|
| 3,525,332 | 8/1970 | Kosaka | 600/178 |
| 4,710,807 | 12/1987 | Chikama | 600/180 |
| 4,924,856 | 5/1990 | Noguchi | 600/178 |
| 5,007,408 | 4/1991 | Ieoka | 600/180 |

*Primary Examiner*—John P. Leubecker
*Attorney, Agent, or Firm*—Snider & Associates; Ronald R. Snider

[57] ABSTRACT

A light source device for an endoscope is capable of selecting a reading method between a method utilizing a light shading period and a method doing without a light shading period. It is possible to adopt both the new reading method and the conventional reading method. A rotary shutter is composed of, for example, a disk with a light passing portion for securing a light source path and a light shading portion formed on the outer peripheral portion, and a DC motor rotates and stops the rotary shutter. When the electronic endoscope apparatus to which the light source device is applied is of an all-pixels reading type, the rotation mode in which light is output during a predetermined light shading period at intervals of $\frac{1}{30}$ sec is set. When the light source device is applied to a conventional electronic endoscope apparatus, for example, of a pixel mixture signal reading type system, the stop mode in which the illuminating light is not shaded is set. The reading system adopted by the electronic endoscope apparatus is judged by an ID discriminator, and the rotary shutter is stopped at a predetermined position by a stop controller in the stop mode.

4 Claims, 5 Drawing Sheets

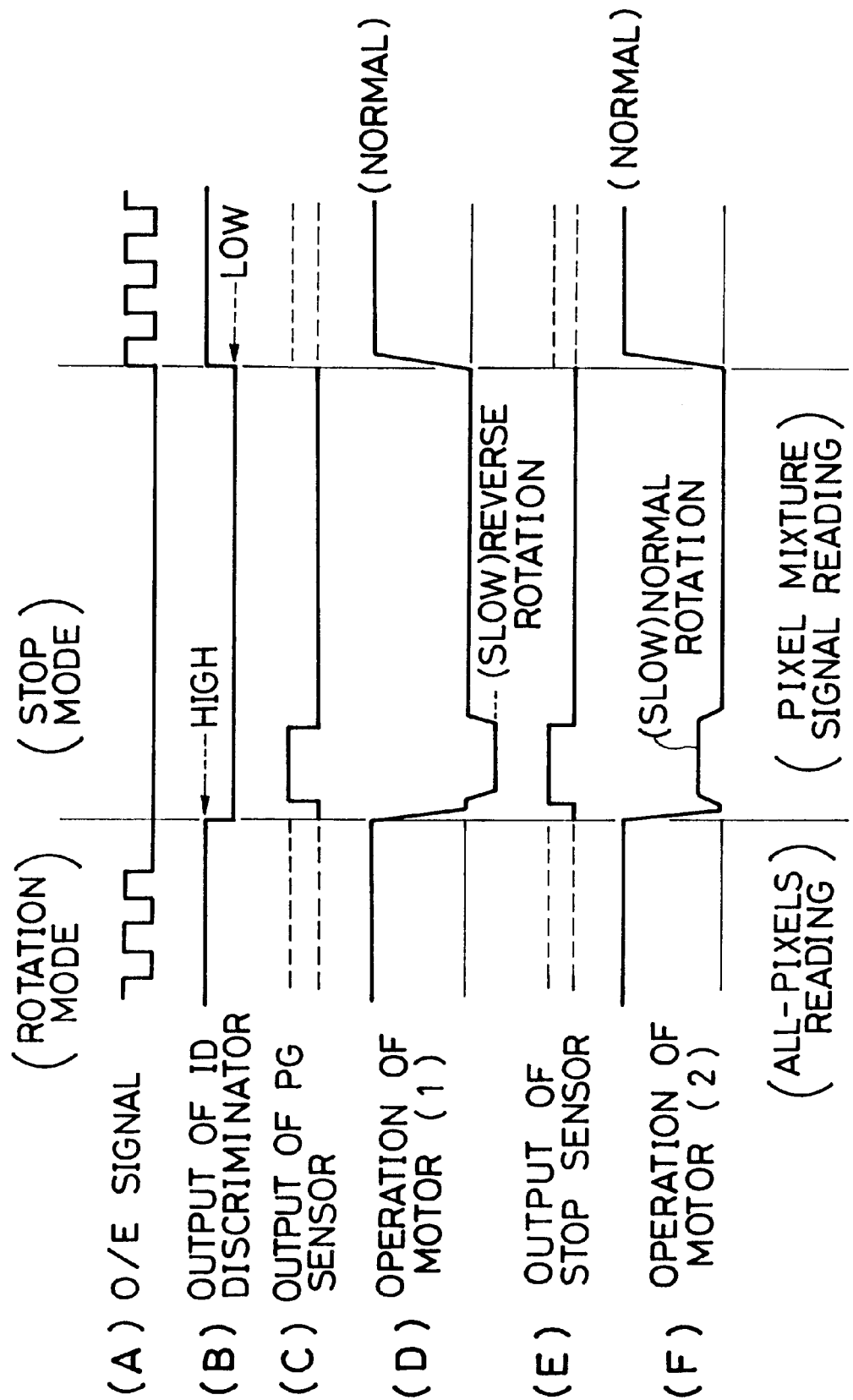

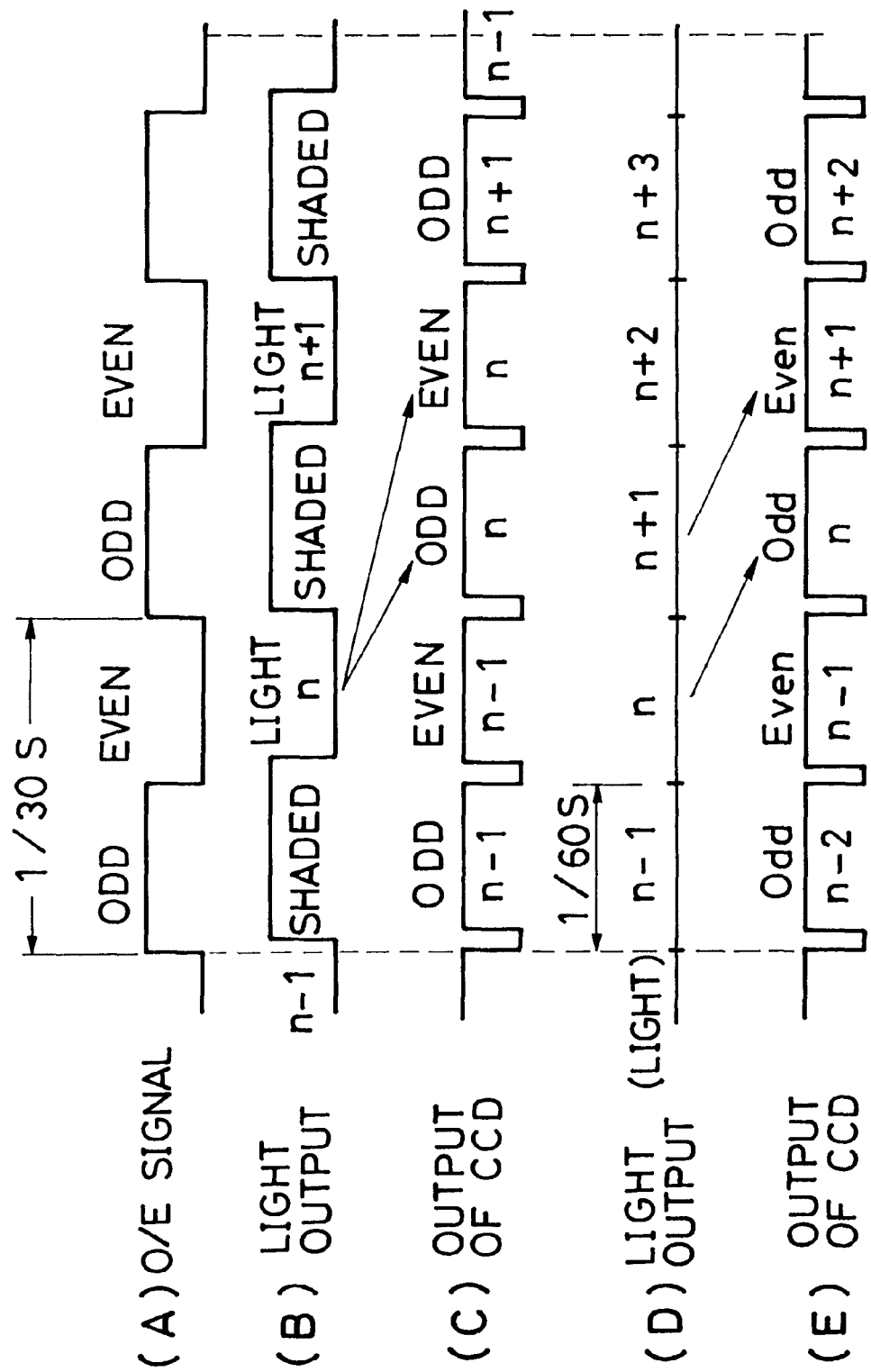

ns No. 8-299712 filed on Oct. 23, 1996 which is
LIGHT SOURCE DEVICE FOR ENDOSCOPE WHICH IS CAPABLE OF LIGHT SETTING SHADING PERIOD

BACKGROUND OF THE INVENTION

This application claims the priority of Japanese Patent Applications No. 8-299712 filed on Oct. 23, 1996 which is incorporated herein by reference.

1. Field of the Invention

The present invention relates to a light source device for an endoscope which is capable of shading illuminating light for a predetermined period and the structure of an electronic endoscope for medical and industrial use which is provided with such a light source device.

2. Description of the Related Art

An endoscope is an apparatus for irradiating illuminating light from a light source into an object of observation such as a body cavity so as to observe the interior of the object. A CCD (Charge Coupled Device) is mainly used as an image sensor. In the CCD, a video signal is obtained by reading an electric charge stored for each pixel by a photoelectric transducer, and it is possible to display the image of the interior of the object of observation by processing the video signal.

When a video signal is read out of the CCD, a pixel mixture signal reading method, for example, is adopted.

In the pixel mixture signal reading method, the charges stored in the CCD during an exposure of 1/60 sec (vertical scanning period) are read while the upper and lower picture data are added, and these signals form one field picture.

In the pixel mixture signal reading method, however, since the upper and lower pixel data are added and mixed, as described above, the resolution in the vertical direction is approximately ½. That is the vertical resolution is lowered. In addition, since the field information in the odd and even fields obtained every 1/60 sec constitute one frame picture (1/30 sec), if a blur is caused by a movement of the object or the endoscope itself, the picture quality is unfavorably deteriorated.

SUMMARY OF THE INVENTION

Accordingly, it is an object of the present invention to eliminate the above-described problems in the related art and to provide a light source device for an endoscope which is capable of setting a light shading period and selecting a reading method between a method utilizing a light shading period and a method doing without a light shading period so as to be applicable to an endoscope apparatus of either system.

This will be explained in more detail. In order to improve the picture quality, it is favorable to adopt a method of reading all the pixels obtained during one exposure without adding the upper and lower picture data. For example, when the pixel data are stored in the CCD during one exposure, all the data on the odd lines are first read, and all the data on the even lines are subsequently read. Thereafter, the data on the odd lines and the data on the even lines are processed and temporarily stored in a memory as the odd field data and the even field data for a picture. The data on the odd lines and the data on the even lines are alternately read out of the memory and sequentially processed as signals, thereby sequentially obtaining a frame picture having a high resolution. Alternatively, all the pixel data may be sequentially read out without being separated into those on the odd lines and those on the even lines.

In the case of extracting video signals by the all-pixels reading method, it is possible to adopt a method of increasing the reading speed (e.g., to twice the speed), but this method requires a CCD having a complicated structure (vertical CCD, etc.) and doubles the clock frequency, so that there is a problem in the cost.

Therefore, the present invention provides a light source device which is capable of setting a light shading period alternately with a lighting period so as to read all the pixels at the same reading speed as in a conventional apparatus in the period including the light shading period.

If the light source device is produced exclusively for an all-pixels reading type endoscope apparatus, it is impossible to connect a conventional electronic endoscope to the light source device. In order to reduce the cost of an electronic endoscope apparatus and enhance the serviceability, it is preferable that the light source device is applicable both to a conventional electronic endoscope apparatus and to a new type of electronic endoscope apparatus.

To achieve this end, in one aspect of the present invention, there is provided a light source device for an endoscope comprising: a rotary shutter which is freely rotatable and which includes a light passing portion for passing the light from a light source therethrough and a light shading portion for shading illuminating light; a motor for driving the rotary shutter; and a controller for controlling the motor so as to rotate the rotary shutter in a rotation mode in which the illuminating light is output every after a predetermined light shading period and to stop the rotary shutter in a stop mode in which the illuminating light is output through the light passing portion without being shaded.

According to this structure, the rotary shutter is provided with the light passing portion in approximately half (180 degrees) of the peripheral portion, for example, and the light shading portion in the remaining area. In the rotation mode, the rotary shutter is so controlled as to rotate once every 1/30 sec. Therefore, in this case, the light is alternately output and shaded every 1/60 sec. In the stop mode, the rotary shutter is stopped at the position where the light passing portion secures the light source path so that the illuminating light is constantly output.

In a light source device for an endoscope provided in another aspect of the present invention, it is judged whether the electronic endoscope apparatus to which the light source device is applied adopts an all-pixels reading system for reading all the pixel data by utilizing the light shading period in the rotation mode or a conventional reading system for reading field data in the stop mode, and the rotation mode or the stop mode is set in accordance with the judged system.

According to this structure, the rotation mode or the stop mode is selected and set in accordance with the information for identifying the reading system of the electronic endoscope. When the rotation mode is set, it is possible to read predetermined pixels, for example, the data on the odd lines and the data on the even lines from a CCD during a period when light is shaded by the light shading portion, thereby enabling all the pixels to be read. When the stop mode is set, illuminating light is constantly output in the same way as in a conventional apparatus, thereby enabling the field data to be sequentially read by a pixel mixture signal reading method, for example.

In still another aspect of the present invention, there is provided a light source device for an endoscope comprising: a light source for projecting illuminating light to an object of observation; a rotary shutter which is freely rotatable and which includes a light passing portion for passing the light from the light source therethrough and light shading portion for shading the illuminating light; a motor for driving the rotary shutter; a detective sensor for detecting the rotating position and the stopping position of the rotary shutter; and a controller for controlling the motor on the basis of the output of the detective sensor so as to rotate the rotary shutter in a rotation mode in which the illuminating light is output every after a predetermined light shading period and to stop the rotary shutter in a stop mode in which the illuminating light is output through the light passing portion without being shaded.

BRIEF DESCRIPTION OF THE DRAWINGS

FIG. 3 is a timing chart of the operation of the light source device shown in FIG. 1;

FIG. 4 is a timing chart of the video signal processing operation in an all-pixels reading system and in a pixel mixture signal reading system in the embodiment;

DESCRIPTION OF THE PREFERRED EMBODIMENT

Figure 1:
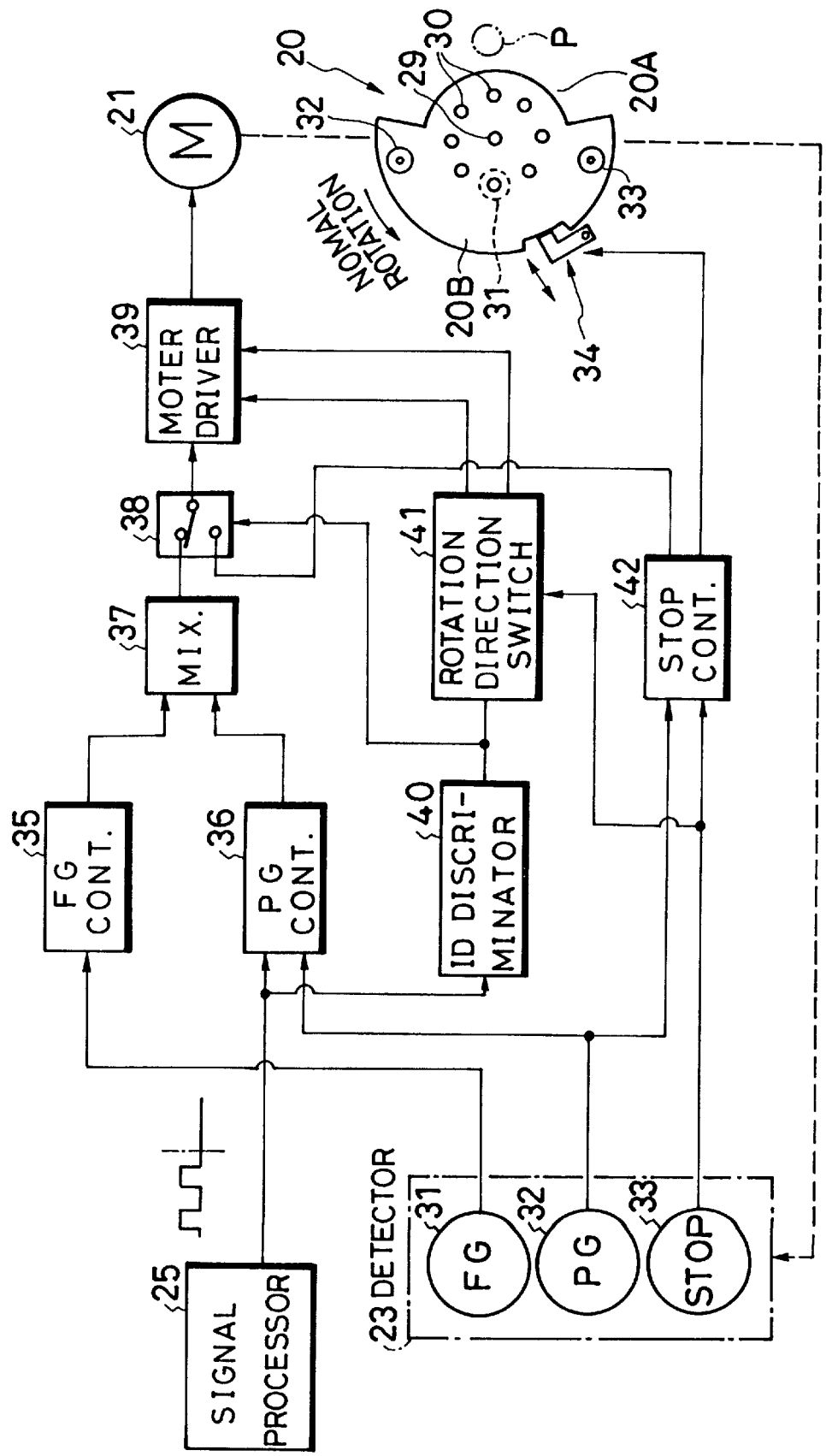
FIG. 1 is a block diagram of the structure of an embodiment of a light source device for an endoscope according to the present invention.
Figure 2:
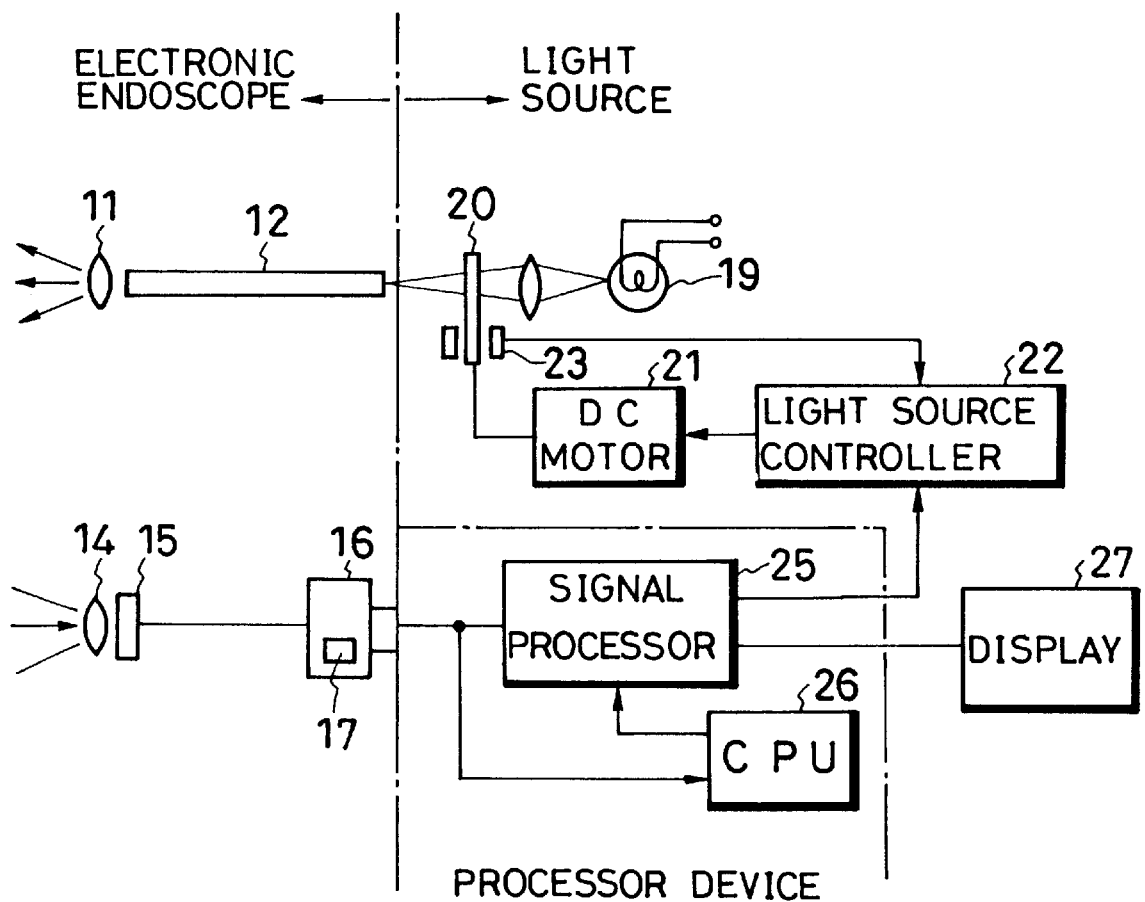
FIG. 2 is a block diagram of the structure an electronic endoscope apparatus applying the light source device shown in FIG. 1.

FIG. 1 shows the structure of an embodiment of a light source device for an endoscope according to the present invention, and FIG. 2 shows the structure of an electronic endoscope apparatus applying the light source device shown in FIG. 1. The structure of the electronic endoscope apparatus will first be explained. As shown in FIG. 2, the electronic endoscope apparatus is provided with an electronic endoscope as a scope, a light source device and a processor device. The electronic endoscope is provided with a light guide 12 for introducing light to an irradiation lens 11, and the light guide 12 is connected to the light source device through a connector.

A CCD 15 is connected to an objective optical system 14 for observation and a connector circuitry portion 16. The connector circuitry portion 16 includes a CCD driving circuit such as a first signal processor for executing processing such as the amplification of video signals and a scope ID signal generator 17 for generating a scope ID (identification) signal which is provided with each electronic endoscope.

The light source device is provided with a light source 19 such as a xenon lamp. A rotary shutter 20 is disposed in front of the light source 19. The rotary shutter 20 is composed of one blade so as to realize a steep rise and fall of luminous flux, as will be described later in detail. A DC motor 21 having a low driving noise and a light source controller 22 are connected to the rotary shutter 20. The rotary shutter 20 is provided with a detector 23 for detecting the rotary position. The controller 22 drives the DC motor 21 on the basis of the detection output of the detector 23.

The processor device is provided with a second signal processor 25 for processing video signals and a CPU 26. The second signal processor 25 executes various processings such as white balance control and gamma correction of video signals and supplies final signals to a display 27. The CPU 26 is provided with a filed ID signal generator for generating a field ID signal for identifying the reading system (all-pixels reading system or a pixel mixture signal reading system) by inputting the scope ID signal output from the electronic endoscope. In this embodiment, O(ODD)/E (EVEN) signals (timing signals) for reading signals on the odd lines and on the even lines from the CCD 15 are used as the field ID signal, as will be explained later in detail.

As shown in FIG. 1, the rotary shutter 20 is connected to the DC motor 21 through a rotary shaft 29. A light passing portion 20A for securing a light source path P and a light shading portion 20B are formed on the outer peripheral portion of the rotary shutter 20. The rotary shutter 20 is also provided with detection holes 30 formed at regular intervals and an FG sensor 31 for executing FG (frequency generator) phase. A PG sensor 32 for executing PG phase generator) phase and a stop sensor 33 are disposed at the upper and lower positions, respectively, in such a manner as to clamp the rotary shutter 20. These sensors 31 to 33 are disposed in such a manner as to clamp the shutter blade so as to detect the state in which light passes.

In order to maintain the stop of the rotary shutter 20, a fixing means 34 such as a claw which engages with a groove is provided. Alternatively, various fixing means such as one utilizing an electromagnetic device and one applied to the rotary shaft 29 may be adopted as the fixing means 34.

The light source controller 22 includes an FG controller 35, a PG controller 36, an adder (MIX) 37, a mode switch 38, a motor driver 39, an ID discriminator 40 (mode discriminator) for inputting the field ID signal, a rotation direction switch 41 and a stop controller 42. The FG controller 35 which inputs the detection signal output from the FG sensor 31 controls the rotation frequency of the rotary shutter 20 so as to be stable, and the PG controller 36 which inputs the detection signal output from the PG sensor 32 controls the phase so that the positions of the light passing portion 20A and the light shading portion 20B are in accord with the signal synchronous with the O/E signal.

The ID discriminator 40 is composed of a monostable multivibrator for triggering, for example, at a rise of the O/E signal (field ID signal) and outputting a High-level signal which is set to keep the High-level time for more than $\frac{1}{30}$ sec. The ID discriminator 40 connects the mode switch 38 to the upper side so as to set a rotation mode when the high-level signal is output, while connecting the mode switch 38 to the lower side so as to set a stop mode when the O/E signal is not detected (Low-level time).

The rotation direction switch 41 sets the normal rotation (counterclockwise direction in FIG. 1) when the rotation mode is set, while setting the reverse rotation in the stop mode. The rotation direction switch 41 also switches the reverse rotation over to the normal rotation when a High-level signal is input from the stop sensor 33. The stop controller 42 judges that the rotary shutter 20 is at the stop position, completely stops the DC motor 21 and fixes the stop position by the fixing means 34 when the PG sensor 32 and the stop sensor 33 are shaded by the shutter 20 and there is no detection output.

The operation of the embodiment having the above-described structure will now be explained with reference to FIGS. 3 to 6. In this embodiment, the rotation mode is set in an all-pixels reading system, while the stop mode is set in a pixel mixture signal reading system. In the all-pixels reading system, the O/E signal shown in FIG. 4(A) is used in order to obtain video signals (stored charges) on the odd (ODD) lines and the video signal on the even (EVEN) lines alternately by the CCD 15. The O/E signal is a rectangular wave signal the rise and the fall of which are repeated at intervals of 1/60 sec.

Since the O/E signal is not used in a conventional pixel mixture signal reading system, it is used as a signal indicating that the rotation mode (and the all-pixels reading system) is selected, and the ID discriminator 40 judges whether or not there is an O/E signal. The CPU 26 judges whether the all-pixels reading system or the pixel mixture signal reading system is adopted from the scope ID signal of the electronic endoscope, and outputs the O/E signal to the ID discriminator 40 as a field ID signal indicating the rotation mode when the all-pixels reading system is adopted. When the electron endoscope adopts both the all-pixels reading system and the pixel mixture signal reading system, a field ID signal indicating the system adopted at the current time is output on the basis of a control signal.

When the O/E signal shown in FIG. 3(A) is input to the ID discriminator 40, the High-level signal shown in FIG. 3(B) is output. In accordance with the High-level signal, the mode switch 38 is connected to the adder 37 and the mode is switched over to the rotation mode. In the rotation mode, the motor driver 39 drives the DC motor 21 so that the rotary shutter 20 rotates once every 1/30 sec. This rotation state is detected by the FG sensor 31 and the PG sensor 32.

The outputs of these sensors 31, 32 are supplied to the FG controller 35 and the PG controller 36, and the outputs of the FG controller 35 and the PG controller 36 are, in turn, supplied to the motor driver 39. By the control of the FG controller 35, the rotary shutter 20 is stably rotated in the direction of normal rotation (counterclockwise direction in FIG. 1), and by the control of the PG controller 36, the light shading operation and the light passing operation are accurately repeated at intervals of 1/30 sec in synchronism with the O/E signal shown in FIG. 4(A). That is, control of the open or close position is executed every 1/60 sec, as shown in FIG. 4(B).

In this manner, the light is projected from the light source at intervals of 1/30 sec into the body as the object of observation through the end portion of the electronic endoscope. In the all-pixels reading system of this embodiment, the charges (data) on all the pixels obtained by the CCD 15 are read out during one exposure of not more than 1/60 sec while the data on the odd lines are separated from the data on the even lines. This state is shown in FIG. 4(C). For example, with respect to the data obtained at the n-th exposure shown in FIG. 4(B), the data n on the odd (ODD) lines are read during the next light shading period. At this light shading period, the data n on the even (EVEN) lines rise and the transfer of the output is finished during the next exposure. Since the data 15 on the even lines in the CCD 15 are transferred to a transfer line during the light shading period, there is no trouble in storing charges at the (n+1)th exposure.

Figure 5A:
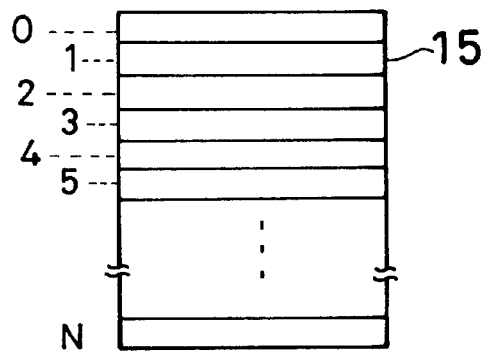
FIGS. 5(A), 5(B) and 5(C) are explanatory views of the picture data obtained in the all-pixels reading system in the embodiment.
Figure 5B:
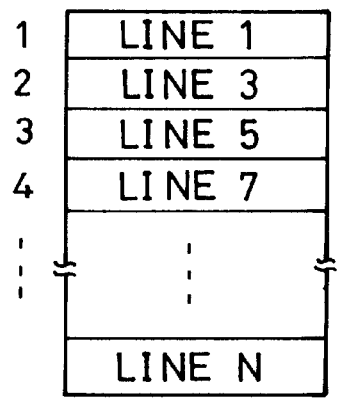
Figure 5C:
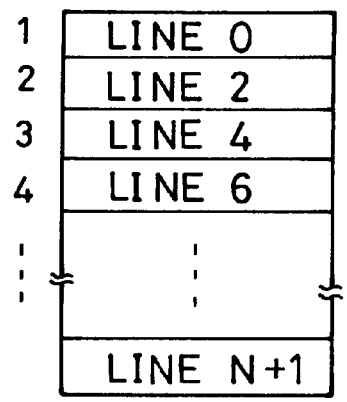

FIG. 5 shows the picture data in the all-pixels reading system. The picture data on the odd lines and on the even lines in the CCD 15 shown in FIG. 5(A) are read separately from each other and after they are subjected to a predetermined processing for forming a picture, they are displayed on the display 27. The data on the odd lines and on the even lines may be processed as the data in the odd field and in the even field as they are. In this case, the vertical resolution is advantageously enhanced as compared with that in a conventional pixel mixture signal reading system. A picture with a high vertical resolution is obtained by temporarily storing the data on the odd and even lines in a memory, alternately reading the data on the odd and even lines, and sequentially forming and processing signals. In addition, since all the pixel data obtained during one exposure by the rotary shutter 20 are processed, it is possible to reduce the deterioration of a picture quality due to a blur caused by a movement of the object or the endoscope itself.

When the pixel mixture signal reading system is adopted, the O/E signal shown in FIG. 3(A) is not supplied to the ID discriminator 40, so that the ID discriminator 40 outputs a Low-level signal, as shown in FIG. 3(B). The mode switch 38 is therefore connected to the stop controller 42, so that the mode is switched over to the stop mode, and the motor 21 is stopped.

In the stop mode, the position of the light passing portion 20A of the rotary shutter 20 is adjusted to the light source path P. More specifically, in the stop mode, if the rotation direction is switched over to the direction of reverse rotation (clockwise direction in FIG. 1) by the rotation direction switch 41, the light shading portion 20B (shutter blade) does not exist at the position of the PG sensor 32, and the output of the PG sensor 32 is at a High level when the motor 21 is stopped, as shown in FIG. 3(C), the DC motor 21 rotates reversely at a slow speed, as shown in FIG. 3(D).

On the other hand, when the light shading portion 20B does not exist at the position of the stop sensor 33, and the output of the stop sensor 33 is at a High level, as shown in FIG. 3(E), the rotation direction switch 41 switches the direction over to the direction of normal rotation, and the DC motor 21 rotates normally at a slow speed, as shown in FIG. 3(F), on the basis of the output of the stop controller 42. When the rotary shutter 20 is at the opposite position to that shown in FIG. 1, and the PG sensor 32 and the stop sensor 33 are shaded (the outputs are Low-level signals), this state is judged by a Low-level signal finally output by the PG sensor 31. In this case, it is also possible to control the rotary shutter 20 to the stop position by reversely rotating the DC motor 21.

When the rotary shutter 20 is disposed at the position shown in FIG. 1, the fixing means 34 is operated under the control of the stop controller 42 so that the claw engages with the groove in order to restrain the rotation of the shutter 20. In this manner, the rotary shutter 20 is set at the position at which the light passing portion 20A secures the light source path P, so that the light from the light source is constantly projected into the body as the object of observation.

FIG. 4(D) shows the state in which the light is output from the light source. In the pixel mixture signal reading system, the data obtained at one exposure of 1/60 sec in the CCD 15 are read as the pixel mixture signals for the information on the odd field and the even field, as shown in FIG. 4(E).

Figure 6:
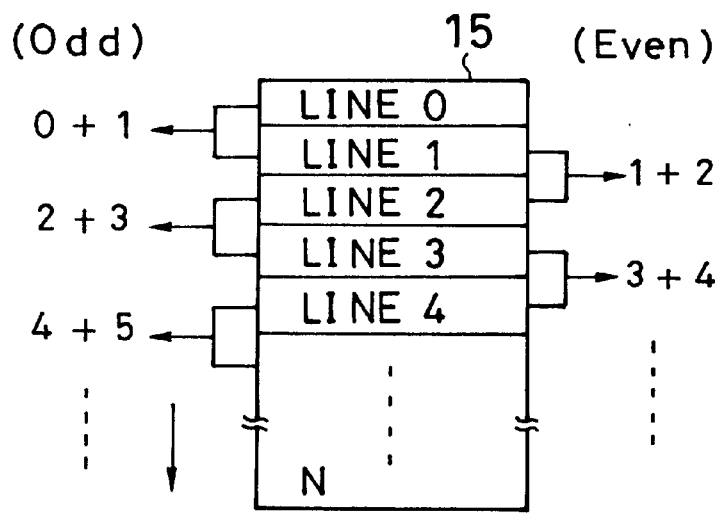
FIG. 6 is an explanatory view of the picture data obtained in the pixel mixture signal reading system in the embodiment.

FIG. 6 shows the picture data in the pixel mixture signal reading system. For example, odd (Odd) field signals such as (line 0+line 1) and (line 2+line 3) and the even (Even) field signals such as (line 1+line 2) and (line 3+line 4) are read out. These video signals are subjected to a predetermined processing, and displayed on the display 27.

As explained above, according to the present invention, it is possible to use the same device and to select a reading method between a method utilizing a light shading period and a method doing without a light shading period. In other words, it is possible to adopt both the new reading method and the conventional reading method. In an electron endoscope apparatus, it is possible to process video signals by the all-pixels reading system when the rotation mode is set, while processing video signals by the mixture signal reading system when the stop mode is set. That is, the light source device according to the present invention is advantageous in that it is applicable to both an electron endoscope adopting an all-pixels reading system and a conventional type of electron endoscope.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. An electronic endoscope which is capable of setting a light shading period, said endoscope comprising:

a image processing means based on an all-pixels reading system that can obtain frame of an image by reading odd lines data and evens lines data of all pixels data formed with an image pickup device by a simultaneous exposure using a light shading period;

a conventional image processing means based on a pixel mixture reading system that can read a mixture of vertical pixels from said image pickup device by a single exposure to obtain one field of an image;

a light source for projecting illuminating light to an object of observation;

a rotary shutter which is freely rotatable and which includes a light passing portion for passing light from a light source therethrough and a light shading portion for shading illuminating light;

a motor for driving said rotary shutter;

a judgement means for judging whether said endoscope has adopted either said all-pixels reading system or said pixel mixture reading system; and a controller executing a rotation mode to set said light shading period at the light shading portion of said shutter by rotating said rotary shutter when it judges that said all-pixels reading system has been selected, and executing a stop mode to supply the light emitted through the light passing portion of said shutter by stopping said rotary shutter when it judges that said pixel mixture reading system has been selected.

2. An electronic endoscope which is capable of setting a light shading period according to claim 1, wherein said rotary shutter is a circular member for shading said light from said light source at the peripheral portion thereof, and a cutaway portion is formed as said light passing portion in approximately half of said peripheral portion.

3. An electronic endoscope which is capable of setting a light shading period according to claim 1, wherein said light shading period is the period for reading one field of image data.

4. An electronic endoscope which is capable of setting a light shading period according to claim 1 wherein charges stored in a CCD when using the pixel mixture reading system are read while upper and lower picture data are added.

* * * * *